(12) United States Patent
Schell

(10) Patent No.: US 6,588,250 B2
(45) Date of Patent: Jul. 8, 2003

(54) AUTOMATIC CALIBRATION MODE FOR CARBON DIOXIDE SENSOR

(75) Inventor: Michael B. Schell, Santa Barbara, CA (US)

(73) Assignee: Edwards Systems Technology, Inc., Cheshire, CT (US)

( * ) Notice: Subject to any disclaimer, the term of this patent is extended or adjusted under 35 U.S.C. 154(b) by 0 days.

(21) Appl. No.: 09/842,622

(22) Filed: Apr. 27, 2001

(65) Prior Publication Data

US 2002/0157447 A1 Oct. 31, 2002

(51) Int. Cl.[7] .................................................. G01N 1/22
(52) U.S. Cl. ........................................................ 73/1.06
(58) Field of Search ................................. 73/1.06, 1.07; 340/632, 526

(56) References Cited

U.S. PATENT DOCUMENTS 5,959,188 A * 9/1999 Duetsch et al. ............... 73/1.06
5,969,223 A * 10/1999 Nagai et al. ................. 73/1.06

FOREIGN PATENT DOCUMENTS

GB 2138949 * 10/1984 ................. 73/1.07

* cited by examiner

*Primary Examiner*—Robert Raevis

(57) ABSTRACT

An automatic calibration mode for a carbon dioxide sensor is based on using a zero gas. The sensor is designed to recognize a distinctive rate of change pattern of carbon dioxide concentrations that would be indicative of a zero calibration routine. This approach can be used for other infrared sensors.

24 Claims, 5 Drawing Sheets

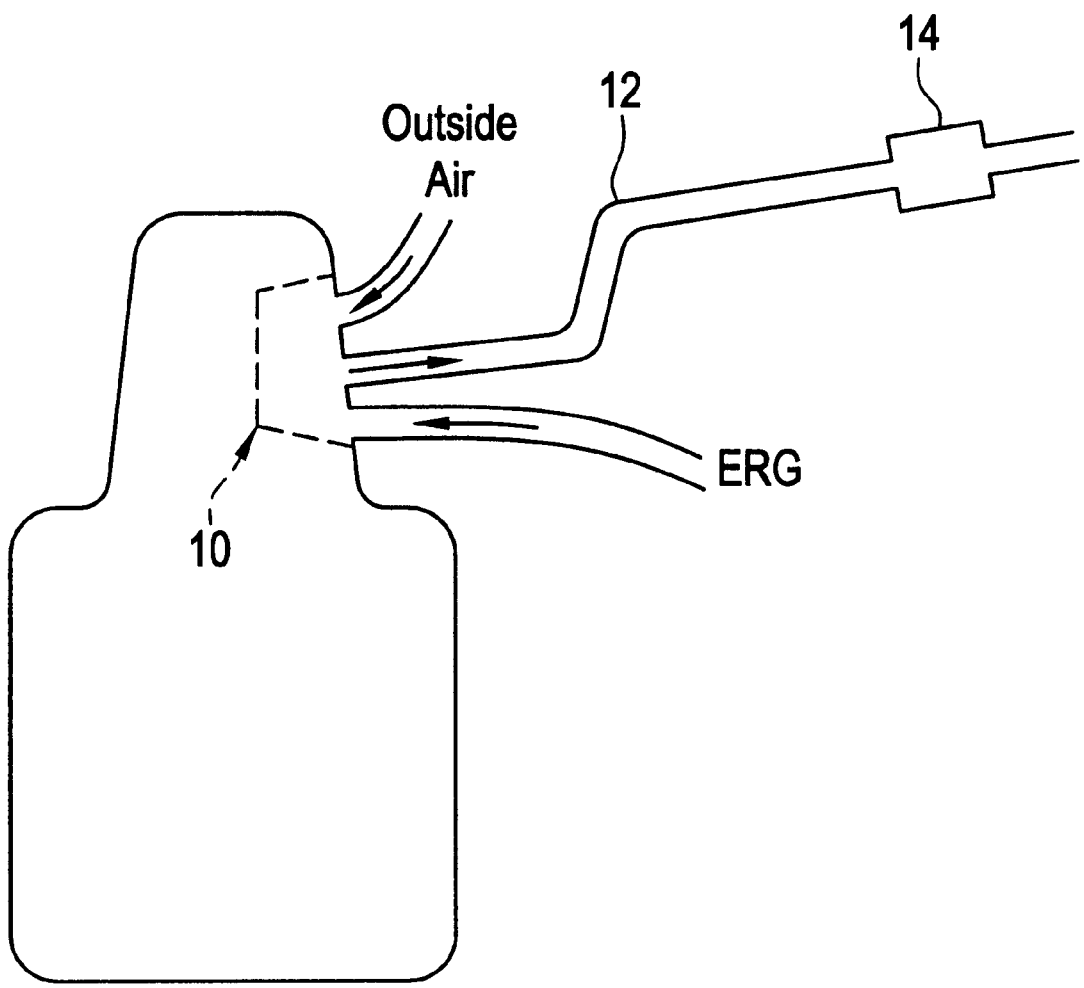

AUTOMATIC CALIBRATION MODE FOR CARBON DIOXIDE SENSOR

PRIORITY

This application is related to application Ser. No. 09/004,142, entitled "Method for Detecting Venting of a Combustion Appliance Within An Improper Space", filed Jan. 7, 1998, the disclosure which is incorporated herein by reference.

FIELD OF THE INVENTION

The present invention relates generally to the field of sensor technology. More specifically, the present invention relates to the development of various infrared (IR) gas sensor technology applications in connection with carbon dioxide sensing, particularly as to measuring/controlling exhaust gas recirculation (EGR) to diesel engines.

BACKGROUND OF THE INVENTION

To acquire desired information of any kind, measurements of physical parameters must be made. Devices that permit these measurements are broadly categorized as sensors. The term "sensors" encompasses a broad range of technologies and devices that respond to a physical stimulus (i.e. light, heat, sound, pressure, magnetism or a particular motion) and transmit a resulting impulse, generally for measurement or operating a control.

Sensors are widely used in many different applications. Some can be as simple as the direct measurement of a thermocouple, or as complex as all-weather imaging systems. Whatever the complexity of the sensor, an interaction between the sensor and its physical environment produces some kind of signal that ultimately leads to the desired information.

In many instances, sensor technology has become a basic enabling technology. The rapid increase in the interest in sensors has been driven by numerous applications, such as analysis of selected compounds in blood, in which sensors can provide a large public benefit.

In addition, sensors are of great importance in safety-related areas, with applications ranging from assessing the integrity of aircraft to fire safety monitoring. Common research and technology issues in these diverse applications include the interpretation of spectral signatures in terms of quantities of interest, such as concentrations, temperatures or thermal properties.

For example, market demand in gas measurement platforms for determining concentration levels of carbon dioxide, is driving increased activity in $CO_2$ technology because in part of its utility in understanding and monitoring ventilation and Indoor Air Quality (IAQ). Building codes and standards governing ventilation in buildings, such as ASHRAE (American Society of Heating Air Conditioning and Refrigeration Engineers) Standard 62-99, have established minimum volumetric outside air requirements on a per-person basis.

Because individuals generally exhale a predictable amount of carbon dioxide, one application is to use this parameter to sense occupancy. An increasing or decreasing level of carbon dioxide can indicate ingress or egress of an indoor zone.

In addition, because outside levels are very low and constant, an indoor measurement can also provide a dynamic measure of the number of occupants of the space and the amount of low concentration outside air being introduced to dilute contaminant concentrations. As a result, a carbon dioxide measurement in a space can be used to measure or control per-person ventilation rates within a space.

Thus, while carbon dioxide is not a direct measure of indoor air quality, it has the potential to be an excellent measure of effective ventilation (mechanical ventilation plus infiltration). Generally, the higher the carbon dioxide concentration, the lower the ventilation. In other words, when indoor carbon dioxide levels are very high (i.e. above 1800 ppm) and ventilation is low (below 7 cfm/person), these conditions can allow contaminants to build up, causing irritation and discomfort.

Determining concentration levels of carbon dioxide is a powerful facility that can be useful in homes, office buildings, schools, and other commercial environments. However, implementable applications are limited by manufacturing and other costs, as well as health, safety, quality and other issues.

For example, in health and safety applications, oxygen sensors have been used to measure depletion of oxygen. However, oxygen sensors are not only expensive, but generally require periodic replacement or recalibration. Thus, it would be desirable to have an inexpensive alternative sensing method of measuring oxygen depletion.

In the automotive industry, there is also an increasing need for carbon dioxide sensor technology to improve the quality, safety and comfort of automobiles. For instance, it is known that the carbon dioxide concentration in the combustion air to an engine can be used to determine the amount of exhaust gases being re-introduced to the engine's combustion air. This is because the carbon dioxide concentration of the engine exhaust is significantly higher than ambient air (i.e. 9 percent versus 350–550 ppm).

However, conventional sensing approaches for gases in engines utilize in-situ sensors that are directly exposed to the stream of gas being measured. Exposing these types of sensors to the harsh engine environment, particularly high temperatures, impairs sensing quality and results. Thus, it would be desirable to have an alternative sensing approach, to determine carbon dioxide concentrations, that could endure the harsh environment in the engine and still produce accurate measurements.

An equally important driver in the automotive industry is the incorporation of sensors into automotive products that aid in extending human life and improving safety. In one instance, there is a need to sense the presence of an individual within a vehicle's trunk in order to prevent unwanted or accidental confinement that could lead to death.

In the area of sensor recalibration, there is an increasing need for sensors with an automatic calibration mode feature that has a fast recalibration time, and provides stable, false-free readings.

Accordingly, there is a need for an inexpensive sensor technology control approach that can be used as an indicia of concentration level characteristics of carbon dioxide. In addition, there is a need for a control approach that is suitable (i.e. standardizable) across a number of different applications.

SUMMARY OF THE INVENTION

The foregoing and other needs have been satisfied to a great extent by the present invention, which includes a very reliable method of determining concentration levels of gases, such as carbon dioxide.

More specifically, the present invention is achieved by use of a gas measurement criterion based on measuring the rate of change of carbon dioxide concentration and variations thereof, using optical methods. Optical methods are the most accurate and reliable method for measuring carbon dioxide because of its inert nature; carbon dioxide reacts poorly with other gases, and is difficult to measure reliably with sensors that depend on physical or chemical reactions.

In one aspect of the present invention, a method of measuring oxygen depletion is employed using the rate of change of carbon dioxide as a surrogate indicator of the amount of oxygen being depleted or displaced in the air. Depletion of oxygen can be measured in one of two instances.

In a first instance, if oxygen is being displaced by carbon dioxide, the natural consequence is that carbon dioxide will have to rise to very high levels to displace a significant amount of oxygen (e.g. greater than 30,000 ppm or 3 percent of $CO_2$).

Conversely, and in a second instance, if oxygen is being displaced by another gas, then it follows that concentrations of carbon dioxide will ultimately begin to drop below normal atmospheric levels of 350–450 ppm. If the rate of fall of $CO_2$ levels drops to below 300 ppm within 24 hours or less, for example, such a drop is reasonably indicative of oxygen depletion, and a warning or control is triggered.

More accurate control levels can be established given known space volume information. Also, the rate of change of carbon dioxide can be used if the rate of change exceeds normal rates that could be expected to be generated by human occupants.

In another aspect of the invention, a carbon dioxide sensor is remotely configured in an automotive or diesel engine in order to measure and control exhaust gas recirculation (EGR) to diesel engines. EGR techniques are used to reduce the emission of certain pollutants, such as nitrogen oxide (NOX), to meet EPA or other environmental requirements.

In order to maintain optimum operating conditions of the engine, and at the same time reduce emissions such as NOX, the ratio of exhaust gasses recirculated into the engine air intake to fresh outside air introduced to the engine, must be relatively constant. Maintaining this ratio can be difficult because of the varying operating speed and corresponding combustion air requirements of the engine.

This ratio may vary with engine design, but typically is approximately 20 to 25 percent EGR to fresh air. Since outside air has very low concentrations and engine exhaust has very high concentrations (i.e. 9–12 percent by volume), the carbon dioxide concentration in the mixed air compartment can provide an indication of the outside air to EGR air mixing, and can be used to maintain the appropriate EGR ratio. This approach employs a sampled method to determine carbon dioxide concentrations.

In this approach, a conductive sample tube is installed into the engine's pre-combustion, air-mixing chamber and channels air to a remote $CO_2$ sensor. This chamber is an area where exhaust gases are combined with ambient air before being introduced to the engine for combustion. This chamber may be inside the engine or as part of an assembly attached to the engine.

The conductive sample tube is of sufficient length to allow for additional cooling of the sample so that sampled gas temperatures are less than 50 degrees Centigrade, but not too long as to cause a significant delay in response time. Sampled air from the pre-combustion air-mixing chamber is pushed through by the pressure differential between the chamber (e.g. 1 atmosphere or more) and ambient pressures around the engine.

Optionally and alternatively, this sampling approach can facilitate control strategies for removing particulates, if necessary, that may require filtration. In addition, reducing the temperature of the sample allows for less complex and potentially more inexpensive $CO_2$ sensor technology to be used, by eliminating the need for components and calibration that operate in high temperature environments.

Another feature and advantage of this aspect of the invention is presented if a conditioned sample is used, because it enables easier measurement of other gases, such as NOX, that are more easily measured using optical methods at temperatures below 50° C.

In a third aspect of the present invention, the rate of change of carbon dioxide concentration levels is used to indicate the presence of an individual in an automobile trunk. There are several other sources of carbon dioxide that must be factored into consideration, since these sources may affect an accurate $CO_2$ sensor reading. The two primary sources are: (1) leakage of carbon dioxide exhaust into the trunk compartment, and (2) deliberate injection of carbon dioxide into the trunk compartment to intentionally activate the sensor; perhaps to automatically open the trunk.

To guard against the occurrence of the two above-mentioned conditions, the $CO_2$ sensor of the present invention and its warning/control logic is preferably configured to identify a rate of change of carbon dioxide that may be likely when one or more humans become trapped in a trunk.

Human carbon dioxide production is a function of activity and body size. Thus, an action/control point within the control logic is calculable based on rate of change data involving, for example, possible ranges of carbon dioxide production rates for assumed range or activity level(s). An action/control point within a control logic can also be calculated based on rate of change data, which calculations include, for example, the volume of the trunk; assumptions for air leakage rates for the trunk; and occupant ages.

These calculations preferably provide a carbon dioxide rate of change range in which it could be determined with reasonable accuracy that a human occupant is in the trunk. If the rate of change measured within the trunk falls within the calculated range, desired control or alarm strategies can be activated. Control or alarm strategies may include an indicator light, buzzer, opening of the trunk, flashing lights, sounding horn, and the like. If suspicious $CO_2$ levels were detected outside the desired or predetermined sensing range, an alternative indicator can be activated.

In a fourth aspect of the present invention, an automatic calibration mode for carbon dioxide sensors is provided. Calibration is based on using a zero gas for calibration. This approach can be used for other infrared sensors, besides carbon dioxide sensors, as well.

Given that ambient levels of carbon dioxide are generally 350 ppm or higher, and that carbon dioxide levels tend to change gradually within a space, the $CO_2$ sensor of this aspect of the invention is designed to recognize a distinctive rate of change pattern of carbon dioxide concentrations that would be indicative of a zero calibration routine. Once this distinctive pattern is identified, the sensor is triggered to go into a calibration mode and reset its calibration based on the $CO_2$ concentrations being measured during the calibration mode.

In a preferred embodiment, the distinctive pattern may comprise a dramatic drop of 200 to 300 ppm or more over approximately 15 to 30 seconds in the sensor reading.

Another distinctive pattern may comprise a stable reading for the subsequent 30 seconds, indicating a constant flow of the calibration gas to the sensor. This pattern may optionally activate the calibration mode of the sensor. Provided that carbon dioxide concentration levels remained stable through the calibration period (e.g. 1 to 5 minutes), the sensor may recalibrate itself to zero based on the same gas it is measuring.

There has thus been outlined rather broadly the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein as well as the abstract included below are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 5 is a perspective view of an engine's chamber showing use of a carbon dioxide sensor to measure and control exhaust gas recirculation to a diesel engine, according to another aspect of the present invention.

DETAILED DESCRIPTION OF PREFERRED EMBODIMENTS OF THE INVENTION

Figure 1:
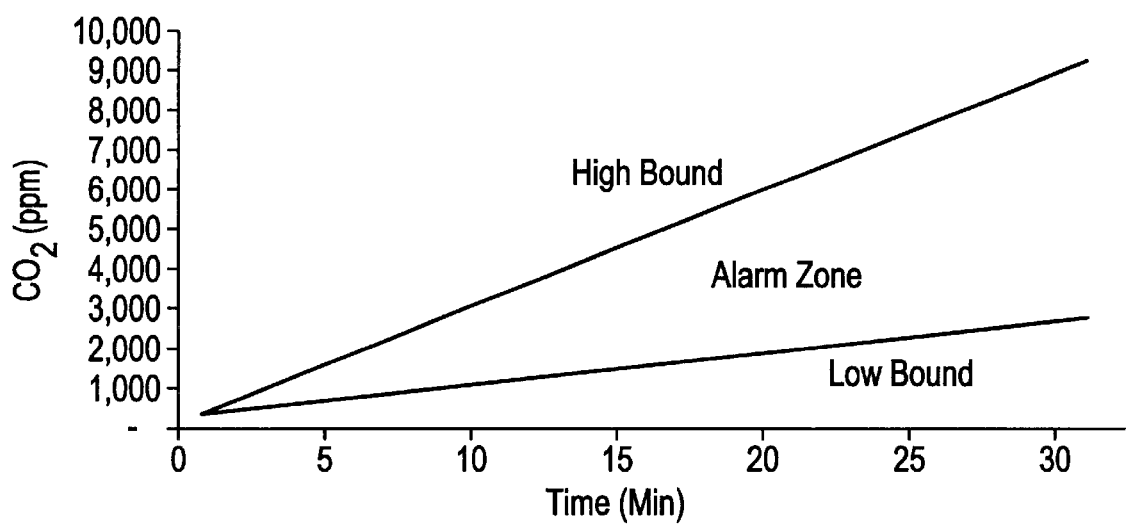
FIG. 1 is a graph plotting carbon dioxide concentration values against time, in accordance with the rate of change methodology of the present invention.

Carbon dioxide is present in outside air, but generally at very low concentrations; namely, from approximately 350 to 450 parts per million (ppm). People are the major contributors of carbon dioxide inside buildings, and can contribute enough carbon dioxide to allow levels to rise as high as 3,000 ppm if a space is poorly ventilated. Concentration levels of carbon dioxide can be higher, but such elevated concentrations are unusual under normal circumstances.

Certain characteristics of carbon dioxide concentration in a space can be indicative of health- and/or safety-risk conditions. These characteristics include an achievement of an absolute threshold level, an observed increase of $CO_2$ levels occurring in conjunction with another activity, or a rate of change of $CO_2$ levels over a period of time.

The gas measurement technique of the present invention, employing the rate of change concept to determine concentration levels of gases in a space, finds utility in many different real-life applications. This rationale holds true whether the rate of change methodology is used as a sole criterion or in combination with other measurement techniques.

One aspect of the invention that utilize rate of change as a sole criterion is exemplified in the home. For most common occupancies in residential structures, for example, modeling studies show that humans contribute carbon dioxide levels that will result in $CO_2$ levels of less than a 5 ppm per minute rate of change.

In contrast, similar modeling studies show that a furnace flue (generally containing between 90,000 and 120,000 ppm $CO_2$), if vented directly into a structure, can contribute to a rate of rise of carbon dioxide levels from 20 to 100 ppm per minute, or more. Thus, depending on the location measured and the volume of enclosed space, rates of rise in carbon dioxide concentration is an accurate indicator of the presence of combustion fumes and the like.

It is important to note that a controlled combustion process, such as a furnace, would provide a relatively constant rate of change during operation. This is in contrast to an uncontrolled fire, which would provide a steadily increasing rate of change of carbon dioxide levels as the uncontrolled fire increased in size.

Depending on the volume of the space, rates of rise of carbon dioxide concentration is also an accurate indicator of combustion leaks. For example, a rate of rise of carbon dioxide of over 30 to 50 ppm per minute is indicative of a furnace or fireplace combustion product(s) leaking into the living space of a house. This type of measurement can be made in the general living space of the house, in the furnace room, utility room or in a garage attached to the house. Alternatively and optionally, a carbon dioxide threshold rate of rise level of approximately 25 ppm per minute can be used as the criterion indicative of improper venting.

In accordance with a first aspect of the present invention, the rate of change of carbon dioxide concentration is used as an accurate criterion to indicate the presence of one or more individuals in a space. This criterion could also be useful in detecting the approximate number of people contained within an enclosed container in applications where smuggling of people may be involved. In addition, if the space is a vehicle trunk compartment, the prevention of deaths by humans being trapped in the trunk, mistakenly or otherwise, is another advantageous application of the present invention.

More specifically, to determine rate of change of carbon dioxide concentration characteristics, the Applicant derived a simulation model that considers a number of factors in calculating the resulting $CO_2$ rates of change that occurred over a period of time. The factors include volume of space, air leakage of the space and, if any, other sources of carbon dioxide that may enter the space.

Another set of factors the simulation model takes into account is human carbon dioxide production rates. The rate of carbon dioxide production by humans is related to both the size of the individual, including age, and activity level. For instance, an adult (i.e. ages 14–65) in a resting mode generally produces a constant rate of $CO_2$ at approximately 0.25 liters per minute. Production rates in this range is likely to occur when people are hidden in a confined space. For an individual locked in a car trunk, activity levels would be higher and therefore production rates may range from 0.5 to 1.5 liters per minute.

The rate of change methodology calculation employed in the simulation model of the present invention looks at the increase of carbon dioxide over time taking into consideration, for example: (1) the number of people in the space, and their expected age and activity level; (2) the volume of the space; and (3) any natural or mechanical methods of ventilation that may dilute space concentrations with outside air. These relationships obey the following equation:

$$C_t = [(C_{t-1} + N/V - C_{OA})(1 - A/V)] + C_{OA}$$

where:

$C_t$ = $CO_2$ concentration at time t (ppm);

$C_{t-1}$ = $CO_2$ concentration in previous time period (ppm);

$C_{OA}$ = $CO_2$ concentration in outside air (ppm);

N = $CO_2$ generation rate by human occupants (cfm);

V = space volume (cu. ft.);

A = the volume of dilution air introduced into the space.

Using the equation above, a rate of change profile is developed for a range of probable/desired situations involving the presence of one or more individuals in a space. When the rate of change data is determined for one or all of the above-mentioned situations, a range of $CO_2$ concentration values is developed to indicate what a likely $CO_2$ rate of change level would be for a given trunk or enclosure space.

This range is achieved by calculating low bound and high bound carbon dioxide concentration values for varying changes in, for example, space volume, activity level, outside carbon dioxide level and/or ventilation. When carbon dioxide concentration values are plotted against time, the graph of FIG. 1 is produced. The area between high and low bound values is best described as an alarm zone in which one or more alarm strategies become activated when concentration levels of carbon dioxide falls therein.

Figure 2:
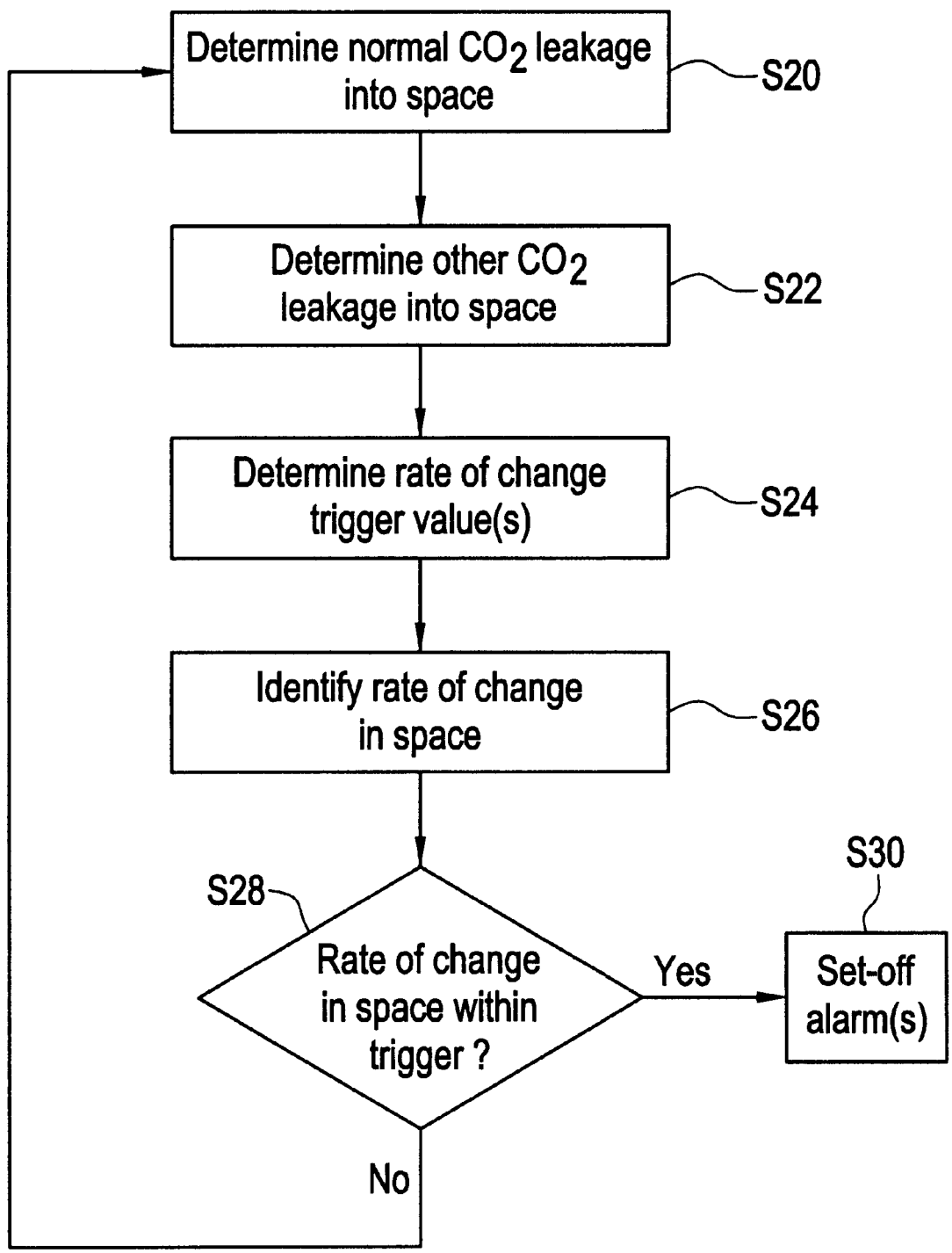
FIG. 2 is a flow chart showing the decision logic for determining the presence of an individual in a space, according to one aspect of the present invention.

Referring now to FIG. 2, there is shown a flow chart of the decision logic describing a process for determining the presence of an individual in a space, using the rate of change methodology of the simulation model of the present invention.

As previously discussed, the process begins with a determination of generally accepted leakage conditions of the space, (Step 20 or S20). In one embodiment, the space comprises a vehicle trunk compartment. In another embodiment, the space may comprise a shipping container or the like. Where the space is an automotive trunk compartment, for example, leakage of carbon dioxide exhaust into a trunk compartment is determined.

Once "normal" leakages have been determined, the next step is to determine or calculate all other appropriate $CO_2$ leakages into the space, (S22). For example, the deliberate injection of carbon dioxide into the trunk compartment may be included in the possibilities of other appropriate leakage conditions, since it may be performed to intentionally activate the sensor to open the trunk. Other such possibilities should be determined.

To guard against the occurrence of these and other possibilities or to prevent unwanted false alarms created by these possibilities, a warning/control logic is preferably configured to incorporate these likely and/or unwelcomed conditions. In essence, the warning/control logic is configured to identify a rate of change of $CO_2$ levels representative of one or more trigger value(s), (S24) such as when one or more humans become trapped in the trunk or enclosure space.

In a preferred embodiment, this identification is accomplished in part by employing one or more action/control point(s), which is/are calculated based on rate of change data. The rate of change data includes calculations on, for example, volume of trunk information; assumptions for air leakage rates for the trunk; carbon dioxide production rates (e.g. exhalation per minute data); ranges of carbon dioxide production possible for an assumed range or activity levels (e.g. low versus high activity level exhalation/minute data); and occupant age (e.g. adult versus a child).

These calculations preferably provide a carbon dioxide rate of change criterion useful for determining with reasonable accuracy the rate of change of carbon dioxide within the space (S26) and ultimately whether a human occupant is in the vehicle trunk compartment or enclosure space.

If the rate of change of carbon dioxide concentration levels within the space falls outside a calculated range, (i.e. the trigger), (S28) the process repeats itself. However, if $CO_2$ concentration rate of change levels falls within the trigger, one or more control or alarm strategies are activated (S30).

In a preferred embodiment, an alarm is sounded if the rate of change of carbon dioxide of at least approximately 50 ppm per minute is detected in the trunk compartment or enclosure space. The alarm may be in the form of an indicator light.

The desired trigger rate-of-change value(s) for generating an alarm signal during a desired period is changeable and very dependent on space volume. For instance, the control or alarm strategy may be used so as not to trigger an alarm upon a single occurrence of detection of a rate of change of carbon dioxide, but only once a rate of change is detected over a consecutive number of times. By not triggering an alarm signal until a rate of change is detected over two or more periods, for example, or even a larger number of periods, such as five or more, the possibility of false alarms can be further minimized.

Alternatively and optionally, different alarm signals may be generated for different trigger value(s). For instance, an initial alarm signal may be generated if a rate of change greater than approximately 5 ppm per minute is detected, a second alarm may be generated if a rate of change greater than approximately 10 ppm per minute is detected, and/or a third alarm generated if a rate of change greater than approximately 25 ppm per minute is detected. Each alarm may take the form of a buzzer, opening of the trunk compartment, flashing lights, sounding horn, and the like.

Audible alarm signals may also be valuable in interpreting why the alarm signal was generated. For example, if suspicious rate of change value(s) were detected outside the sensing range of the trunk compartment, a very low audible alarm signal may be activated to indicate a low existence level.

Figure 3:
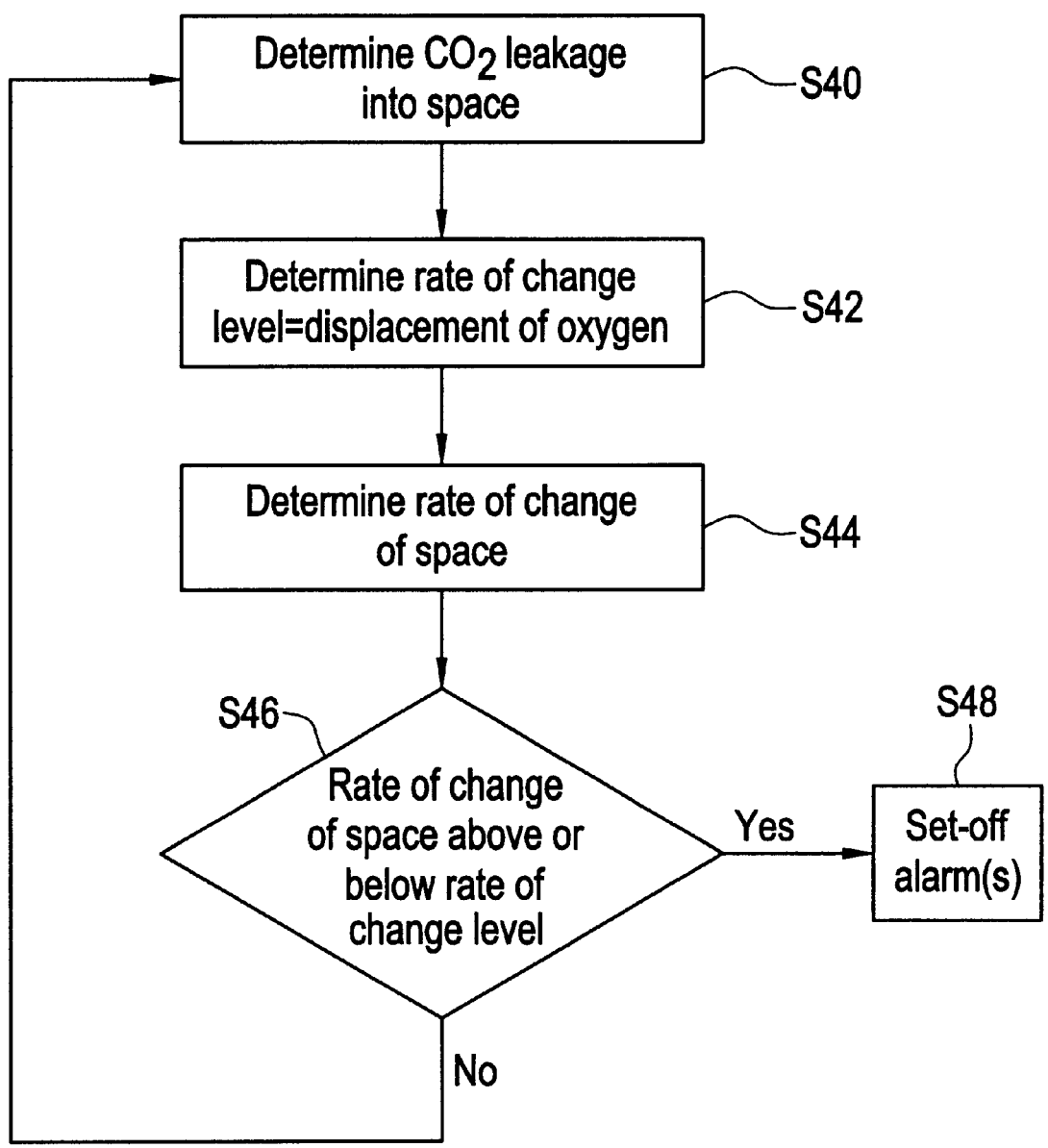
FIG. 3 is a flow chart illustrating the decision logic for determining a condition of oxygen depletion, using a variation of the rate of change methodology of the simulation model of the present invention.

In yet another aspect of the present invention, the above rate of change concept is employed to indicate a condition of oxygen depletion. Referring now to FIG. 3, there is shown a flow chart showing the process for determining a condition of oxygen depletion, using a variation of the rate of change methodology of the present invention. The idea here is to use the rate of change of $CO_2$ concentrations rising above or falling below a level that indicates the displacement of oxygen.

The process begins with a determination of all pertinent carbon dioxide leakage conditions into the space (S40). The space may comprise any variety of enclosure spaces, such as a room in a house, office or commercial building, an auditorium, or the like. Pertinent leakage conditions are user- and situation-definable.

The next step is to determine the carbon dioxide rate of change level that indicates displacement of oxygen (S42). For instance, carbon dioxide would have to rise to very high levels (e.g. >30,000 ppm) in order to observably displace a significant amount of oxygen, if oxygen is being displaced by carbon dioxide.

Alternatively and conversely, concentrations of carbon dioxide dropping at a rate below normal atmospheric levels of 350 to 450 ppm, is preferably indicative that oxygen is being displaced by another gas. Any consistent and sustained drop below these levels would indicate displacement of carbon dioxide. In this fashion, carbon dioxide operates as a surrogate indicator of the amount of oxygen being depleted or displaced in a space.

A subsequent step is to determine the rate of change of carbon dioxide concentration of the space (S44). Note that the above steps need not be performed in the exact sequential order as discussed, just as long as each determination is made prior to Step 46 (S46), which is an inquiry whether the $CO_2$ rate of change of the space is above or below the $CO_2$ rate of change level.

A warning/control logic is also configurable to identify either a carbon dioxide rate of change range or threshold level that is indicative of oxygen displacement. The rate of change data may include the following: volume of space information; assumptions for air leakage rates; carbon dioxide production rates; ranges of carbon dioxide production for assumed ranges or activity levels; and occupant age(s).

Moreover, once an undesired rise or drop has been determined, a warning or control alarm is optionally triggered (S48), as previously discussed. The warning or alarm may take the form of a visible or audible signal.

More accurate control levels can be established given known space volume information. Space volume is a critical factor in calculating rate of change value(s). Also, the rate of change of carbon dioxide concentration can be used if the rate of change exceeds normal rates that could be expected to be generated by human occupants.

Figure 4:
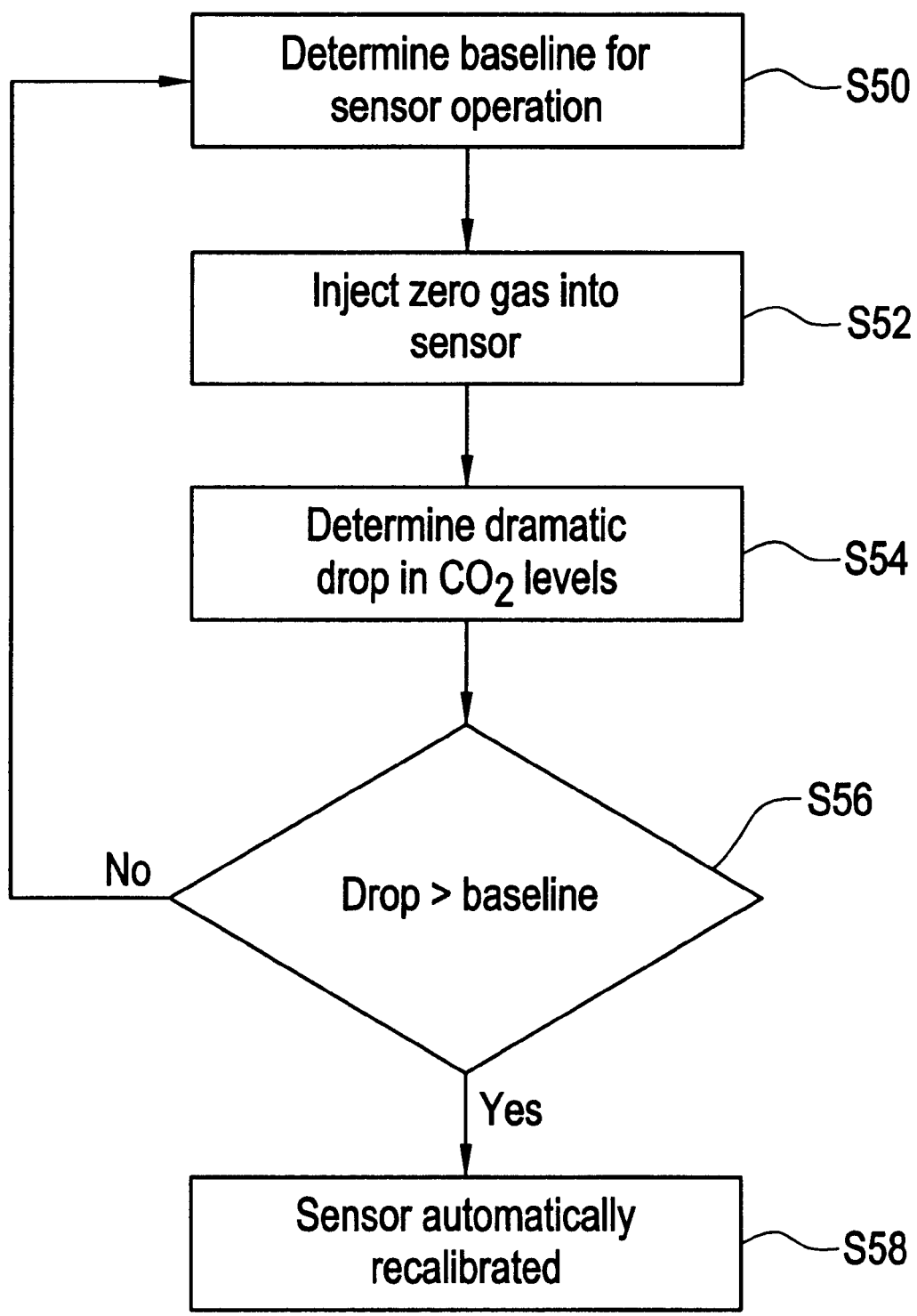
FIG. 4 is a flow chart illustrating the decision logic of an automatic calibration mode for a carbon dioxide sensor, in accordance with another aspect of the present invention.

In yet another aspect of the present invention, an automatic calibration mode for a carbon dioxide sensor is provided. Automatic calibration in carbon dioxide or other infrared sensor is based on using a zero gas for calibration. Referring to FIG. 4, the idea is to inject a zero gas into the sensor (S52), and look for a dramatic drop in carbon dioxide concentrations (S54) below a given or desired baseline for sensor operation (S50). (Atmospheric concentrations of carbon dioxide below 350 ppm ate generally unlikely.) The zero gas is preferably not a gas generally tested by the sensor, such as nitrogen.

The dramatic drop may be determined as desired. In a preferred embodiment, a drop may be determined to be 200 ppm or more over a five-minute period. In other words, if the drop is more than 200 ppm (S56) over the designated or desired time period, the sensor is configured to automatically recalibrate itself (S58) with a microprocessor-driven switch that switches on. In essence, the dramatic drop in sensor reading over the course of five minutes, would be indicative of the zero gas and the sensor would recalibrate that reading to be the zero point.

In another embodiment, the dramatic drop may be determined to be a range at approximately 200 to 300 ppm or more over approximately 15 to 30 seconds in the sensor reading. Alternatively and optionally, the triggering condition may comprise a stable reading for the subsequent 30 seconds, indicating a constant flow of the calibration gas to the sensor. This pattern may optionally activate the calibration mode of the sensor. Provided that carbon dioxide concentration levels remained stable through the calibration period (e.g. 1 to 5 minutes), the sensor may recalibrate itself to zero based on the same gas it is measuring.

A diagnostic routine can also optionally be performed to determine the stability of the reading over a period of time, such as one minute. Preferably, the variation in reading of the measurement should not exceed the background noise of the sensor.

In another aspect of the present invention, the rate of change of carbon dioxide concentration is also measurable in the recirculated air of an engine's precombustion, air-mixing chamber 10. As shown in FIG. 5, chamber 10 is simplified to include those elements pertaining to an easy facilitation of the present invention.

A conductive sample tube 12 is installed into the engine's pre-combustion chamber 10 to channel air from the chamber 10. In chamber 10, exhaust gases are combined with ambient air before introduction to the engine (not shown) for combustion. Also, chamber 10 may be arranged inside the engine or as part of an assembly attached to the engine.

The length of the sample tube 12 is important. In a preferred embodiment, the sample tube 12 is of sufficient length to allow for additional cooling of the sample air, so that sampled gas temperatures are less than 50 degrees Centigrade, but not too long as to cause a substantially significant delay in response time. Sampled air from the chamber 10 is pushed through the tube 12 by the pressure differential between the chamber 10 (i.e. 1 atmosphere or more) and ambient air pressure around the engine.

A carbon dioxide sensor 14 is configured onto the conductive sample tube 12 a distance remote from the chamber 10. By this arrangement, the carbon dioxide concentration in the pre-combustion air to an engine is accurately measured despite the harsh engine environment.

Alternatively and optionally, this arrangement can be useful for removing air particulates, if necessary, that may require filtration. In addition, in cases where the temperature of the sample may be reduced, less complex and therefore more inexpensive, non-temperature-sensitive carbon dioxide sensor technology can be used, because the need for components and calibration that operate in high-temperature environments is eliminated.

Moreover, in other cases where a conditioned sample is used, this arrangement of the present invention may facilitate easier measurement of other gases, such as nitrogen oxide (NOX), that are more easily measured using optical techniques at temperatures below 50 degrees Centigrade. That is, calculation of the NOX level of the exhaust gas can be determined based on the NOX measured in the chamber 10 and the percentage of exhaust gas recirculation (EGR) being introduced to the chamber 10 calculated from carbon dioxide levels. In other words, by keeping the percentage of EGR at a certain amount, the level of NOX can be maintained at no more than a certain level.

It is important to recognize that in measuring the rate of change of carbon dioxide concentration, it is not necessary to measure absolute concentrations. The critical point is the relative change in concentrations. In order to minimize costs, it is contemplated that a Non-Dispersive Infrared (NDIR) sensor be used as the carbon dioxide sensor when practicing an embodiment of the present invention. NDIR detectors responds well to $CO_2$, have better than average sensitivities, and lasts longer than electrochemical detectors.

Accordingly, it would also be possible to use a carbon dioxide detector that relies upon a ratioing technique to determine when a rate of change in carbon dioxide exceeds what would be equivalent to a desired level. A description of a ratioing technique used in an NDIR sensor is set forth in U.S. Pat. No. 5,026,992, the disclosure of which is incorporated herein by reference.

The above description and drawings are only illustrative of preferred embodiments which achieve the objects, features, and advantages of the present invention, and it is not intended that the present invention be limited thereto. It would be readily apparent to those skilled in the art that further changes and modifications in the actual concepts described herein can be readily made without departing from the spirit and scope of the invention as defined in the following claims.

For example, it should be possible to design a single apparatus that could be used to practice the invention that includes various logic options and/or is programmable to reset or revise such logic options. Also, the alarm signal can take on any of a variety of forms, such as an audible or visible warning.

Or the alarm signal could be an electrical signal sent to a device that acts upon receipt of the alarm signal. Thus, for example, generation of the alarm signal could trigger another event, such as turning off the engine of a vehicle or altering its operation. Alternatively, another device or process could be triggered into operation to remove air particulates.

The many features and advantages of the invention are apparent from the detailed specification, and thus, it is intended by the appended claims to cover all such features and advantages of the invention which fall within the true spirits and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for automatic calibration of a carbon dioxide sensor, comprising the steps of:
   determining a baseline carbon dioxide concentration value for sensor operation;
   injecting a zero gas into said sensor;
   determining whether at least one drop in carbon dioxide concentration value occurs below the baseline value over a predetermined time period; and
   activating recalibration of said sensor when said drop in carbon dioxide concentration occurs.

2. The method according to claim 1, further comprising:
   recognizing a predetermined rate of change pattern of carbon dioxide concentrations.

3. The method according to claim 2, further comprising:
   resetting the sensor's calibration, once said predetermined rate of change pattern is identified, based on the carbon dioxide concentration measured.

4. The method according to claim 1, wherein the step of determining the baseline carbon dioxide concentration value for sensor operation is user-definable.

5. The method according to claim 1, wherein the step of determining the drop in carbon dioxide concentration over said predetermined time period is user-definable.

6. The method according to claim 1, wherein said drop is 200 parts per million over a five-minute period.

7. The method according to claim 1, wherein said drop includes a range from 200 to 300 ppm over 15 to 30 seconds.

8. The method according to claim 1, wherein said drop in sensor reading over a five-minute time period is indicative of a zero gas, causing the sensor to recalibrate said reading to be a zero point.

9. The method according to claim 1, wherein the step of activating recalibration includes resetting the sensor's calibration with a microprocessor-driven switch.

10. The method according to claim 1, further comprising:
    performing a diagnostic routine to determine stability of one or more sensor readings over another predetermined period of time.

11. The method according to claim 1, further comprising:
    activating an alarm strategy when the step of activating recalibration occurs.

12. The method according to claim 11, wherein said step of activating an alarm strategy includes activating at least one of a visible and audible alarm.

13. The method according to claim 11, wherein said step of activating an alarm strategy includes activating at least one of a visible and audible alarm upon a single occurrence of resetting of the sensor's calibration.

14. The method according to claim 11, wherein said step of activating an alarm strategy includes activating at least one of a visible and audible alarm upon a stable reading for a 30-second period, said stable reading indicating a constant flow of a calibration gas to said sensor.

15. The method according to claim 1, wherein a variation in sensor reading of said carbon dioxide concentration being measured does not exceed a background noise of said sensor.

16. The method according to claim 1, wherein said zero gas is nitrogen.

17. A system for automatically calibrating a carbon dioxide sensor, said system comprising:
    means for determining a baseline carbon dioxide concentration value for sensor operation;
    means for injecting a zero gas into the sensor;
    means for determining whether at least one drop in carbon dioxide concentration value occurs below the baseline value over a predetermined time period; and
    means for activating recalibration of the sensor when said drop in carbon dioxide concentration occurs.

18. The system according to claim 17, wherein the means for determining the baseline carbon dioxide concentration value for sensor operation allows a user to define said baseline carbon dioxide concentration value.

19. The system according to claim 17, wherein the means for determining the drop in carbon dioxide concentration over said predetermined time period allows a user to define said drop in carbon dioxide concentration over said predetermined time period.

20. The system according to claim 17, further comprising:
    means for activating an alarm strategy when said means for activating recalibration are used.

21. The method according to claim 1, further comprising:
    means for recognizing a predetermined rate of change pattern of carbon dioxide concentrations.

22. An apparatus for automatic calibration of a carbon dioxide sensor, comprising:
    a detector for determining a baseline carbon dioxide concentration value for sensor operation;
    an injector for injecting a zero gas into the sensor, said injector in communication with the sensor;
    a microprocessor, wherein said microprocessor determines whether at least one drop in carbon dioxide concentration value occurs below the baseline value over a predetermined time period, said microprocessor in communication with said detector; and a switch wherein, said switch switches on to activate recalibration of the sensor when said drop in carbon dioxide concentration occurs, said switch being in communication with said microprocessor and the sensor.

23. The apparatus according to claim 22, wherein said detector for determining a baseline carbon dioxide concentration value for sensor operation, accepts user-defined input.

24. The apparatus according to claim 22, wherein the said microprocessor accepts user-defined input.

* * * * *